(12) United States Patent
Kang et al.

(10) Patent No.: US 9,918,647 B2
(45) Date of Patent: Mar. 20, 2018

(54) APPARATUS FOR DETECTING INFORMATION OF LIVING BODY

(71) Applicant: SAMSUNG ELECTRONICS CO., LTD., Suwon-si (KR)

(72) Inventors: Jaemin Kang, Seoul (KR); Younho Kim, Hwaseong-si (KR); Sangyun Park, Hwaseong-si (KR); Hyoyoung Jeong, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 252 days.

(21) Appl. No.: 14/704,424

(22) Filed: May 5, 2015

(65) Prior Publication Data

US 2016/0000339 A1 Jan. 7, 2016

(30) Foreign Application Priority Data

Jul. 4, 2014 (KR) .................. 10-2014-0083903

(51) Int. Cl.
*A61B 5/00* (2006.01)
*A61B 5/021* (2006.01)
*G01L 11/02* (2006.01)

(52) U.S. Cl.
CPC ........ *A61B 5/02141* (2013.01); *A61B 5/0082* (2013.01); *A61B 5/02108* (2013.01); *G01L 11/02* (2013.01); *A61B 2562/0238* (2013.01); *A61B 2562/0247* (2013.01); *A61B 2562/164* (2013.01); *A61B 2562/166* (2013.01); *A61B 2562/227* (2013.01)

(58) Field of Classification Search
CPC .............. A61B 5/02141; A61B 5/0082; A61B 5/02108; A61B 2562/0238; A61B 2562/0247; A61B 2562/164; A61B 2562/166; A61B 2562/227; G01L 11/02
See application file for complete search history.

(56) References Cited

U.S. PATENT DOCUMENTS

| 8,206,309 B2 | 6/2012 | Oh et al. | |
| 2012/0316448 A1* | 12/2012 | Gu | A61B 5/02108 600/499 |
| 2013/0140611 A1* | 6/2013 | Kim | H01L 29/84 257/254 |

(Continued)

FOREIGN PATENT DOCUMENTS

| JP | 2007-209374 A | 8/2007 |
| KR | 10-0643756 B1 | 11/2006 |

(Continued)

*Primary Examiner* — Scott Getzow
(74) *Attorney, Agent, or Firm* — Sughrue Mion, PLLC (57) ABSTRACT

A biometric information detecting apparatus is provided. The biometric information detecting apparatus includes a fixing unit disposed on a lower structure, and a pressure pulse wave measuring unit that is supported by the fixing unit and separate from the lower structure. An optical pulse wave measuring unit is disposed on the pressure pulse wave measuring unit. The optical pulse wave measuring unit may contact a surface of a subject's body. A pressure pulse wave of the subject's body may be measured by the pressure pulse wave measuring unit and an optical pulse wave of the subject's body may be measured by the optical pulse wave measuring unit, at the same time.

20 Claims, 8 Drawing Sheets

(56) References Cited

U.S. PATENT DOCUMENTS

| | | | |
|---|---|---|---|
| 2014/0150571 A1* | 6/2014 | Kuniyoshi | G01L 1/205 73/862.625 |
| 2014/0221772 A1* | 8/2014 | Wolloch | A61B 7/003 600/301 |

FOREIGN PATENT DOCUMENTS

| | | |
|---|---|---|
| KR | 10-0681387 B1 | 2/2007 |
| KR | 10-1432038 B1 | 9/2014 |

* cited by examiner

APPARATUS FOR DETECTING INFORMATION OF LIVING BODY

RELATED APPLICATION

This application claims priority from Korean Patent Application No. 10-2014-0083903, filed on Jul. 4, 2014, in the Korean Intellectual Property Office, the disclosure of which is incorporated herein in its entirety by reference.

BACKGROUND

1. Field

Exemplary embodiments of the present disclosure relate to a biometric information detecting apparatus, and more particularly, to a biometric information detecting apparatus which is capable of measuring an optical signal and a pressure signal from a living body.

2. Description of the Related Art

In view of the public's increased interest in health, various kinds of biometric information detecting apparatuses have been developed. Particularly, various wearable devices, which may be worn directly by subjects, as well as devices specialized in health care, have been developed.

Methods of detecting biometric information, such as a pulse wave, may be largely categorized as invasive methods and noninvasive methods. Noninvasive methods, which may easily detect the pulse wave without causing a pain to a subject, are usually used.

For precise pulse wave analysis (PWA), information based on an optical signal or a pressure signal, measured at a surface of a subject's body, is obtained. The biometric information of the subject may then be obtained based on this information. Various methods are used to reduce measurement errors.

SUMMARY

One or more exemplary embodiments may provide a biometric information detecting apparatus which is capable of measuring an optical pulse wave and a pressure pulse wave at the same time.

One or more exemplary embodiments may provide a biometric information detecting apparatus which is capable of measuring an optical pulse wave and a pressure pulse wave at the same time at the same location on a subject's body.

Additional exemplary aspects will be set forth in part in the description which follows and, in part, will be apparent from the description, or may be learned by practice of the presented embodiments.

According to an aspect of an exemplary embodiment, a biometric information detecting apparatus includes: a fixing unit disposed on a lower structure; a pressure pulse wave measuring unit that is connected to the fixing unit; and an optical pulse wave measuring unit disposed on the pressure pulse wave measuring unit.

An upper surface of the optical pulse wave measuring unit may be configured to directly contact a subject's body.

An upper surface of the optical pulse wave measuring unit may protrude above an uppermost surface of the fixing unit.

The pressure pulse wave measuring unit may be disposed to be separate from the lower structure.

The pressure pulse wave measuring unit may be formed of a flexible material.

The fixing unit may comprise at least one fixing unit respectively connected to at least one end of the pressure pulse wave measuring unit.

The pressure pulse wave measuring unit may comprise pattern portions connected to the one or more fixing units, and the pattern portions may have a straight, linear shape, a curved shape, or a zigzag shape.

The fixing unit may comprise a rigid printed circuit board (RPCB) and the pressure pulse wave measuring unit may comprise a flexible printed circuit board (FPCB).

The fixing unit may comprise a substrate having a hole formed therein, and the pressure pulse wave measuring unit may be connected to an inside wall of the hole.

The pressure pulse wave measuring unit may comprise one or more pattern portions connected to the inside wall of the hole of the fixing unit, and the one or more pattern portions may have a straight, linear shape, a curved shape, or a zigzag shape.

The optical pulse wave measuring unit may be disposed on a central portion of the pressure pulse wave measuring unit; and an optical pulse wave may be measured by the optical pulse wave measuring unit and a pressure pulse wave may be measured by the pressure pulse wave measuring unit, with respect to an identical region of a subject's body, when the optical pulse wave measuring unit contacts the subject's body.

A central axis of the optical pulse wave measuring unit may be aligned in a vertical direction with a central axis of the pressure pulse wave measuring unit.

The optical pulse wave measuring unit may comprise a light-receiving portion and a light-emitting portion.

The optical pulse wave measuring unit may be electrically connected to an optical signal measuring unit via the pressure pulse wave measuring unit.

The optical signal measuring unit may comprise a light-emitting device control portion which is electrically connected to the light-emitting portion and a light-receiving device control portion which is electrically connected to the light-receiving portion.

The light-emitting device control portion and the light-receiving device control portion each may be disposed on the fixing unit.

The fixing unit may comprise a conductive pattern which is configured to receive a bio-signal from the pressure pulse wave measuring unit and the optical pulse wave measuring unit or to supply power to the pressure pulse wave measuring unit and to the optical pulse wave measuring unit.

The fixing unit may comprise the conductive pattern is mounted on an insulating layer.

The fixing unit may further comprise a plug which is connected to the conductive pattern to transmit a signal or to supply power.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Sizes of elements in the drawings may be exaggerated for convenience of explanation. In other words, since sizes and thicknesses of components in the drawings are arbitrarily illustrated for convenience of explanation, the following embodiments are not limited thereto.

Figure 1:
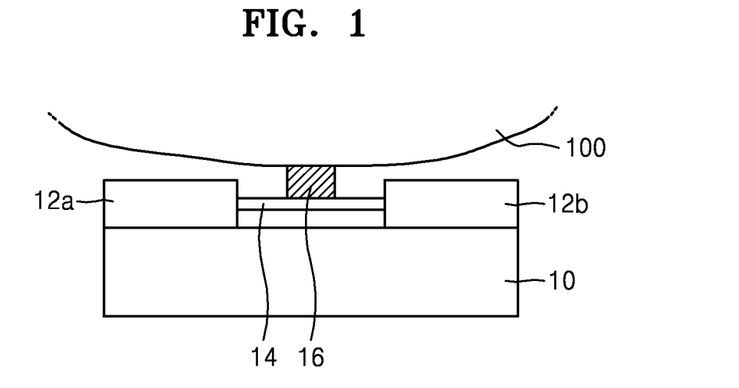
FIG. 1 is a cross-sectional view of a biometric information detecting apparatus according to an exemplary embodiment.

FIG. 1 is a view of a biometric information detecting apparatus according to an exemplary embodiment.

Referring to FIG. 1, the biometric information detecting apparatus may include a lower structure 10, fixing units 12a and 12b disposed on the lower structure 10, and a pressure pulse wave measuring unit 14 that is connected to the fixing units 12a and 12b. Also, an optical pulse wave measuring unit 16 may be disposed on the pressure pulse wave measuring unit 14. The optical pulse wave measuring unit 16 may be disposed on the pressure pulse wave measuring unit 14, such that is protrudes upwards from the pressure pulse wave measuring unit 14. The fixing units 12a and 12b may be connected to respective ends of the pressure pulse wave measuring unit 14.

An upper surface of the optical pulse wave measuring unit 16 may protrude upwards beyond upper surfaces of the fixing units 12a and 12b and may be configured to contact a subject's body 100. When a surface of the subject's body 100 is brought into contact with the optical pulse wave measuring unit 16, biometric information of a portion of the subject's body 100, i.e. the portion contacting the optical pulse wave measuring unit 16, an optical pulse wave and a pressure pulse wave of the portion of the subject's body 100 may be measured at the same time by using the optical pulse wave measuring unit 16 and the pressure pulse wave measuring unit 14.

The lower structure 10 may be a structure in which the biometric information detecting apparatus is set. The lower structure 10 may be any of various wearable devices, such as any of various smart watches or other wearable apparatuses. Alternately, a biometric information detecting apparatus according to this embodiment may be used not only in in a health care device or medical device, as would be understood by one of skill in the art.

The fixing units 12a and 12b may be configured to support opposite ends of the pressure pulse wave measuring unit 14. The fixing units 12a and 12b may include signal-transmitting or power-supplying elements, which may transmit biosignals, measured by the pressure pulse wave measuring unit 14 and the optical pulse wave measuring unit 16, or which may supply, to the pressure pulse wave measuring unit 14 and the optical pulse wave measuring unit, the power necessary for driving these units, respectively.

According to exemplary embodiments, when the subject's body 100 applies pressure to the pressure pulse wave measuring unit 14 via the optical pulse wave measuring unit 16, a pressure pulse wave may be measured by using as an indicator, a warpage of the pressure pulse wave measuring unit 14 which is flexible. Accordingly, in order to accurately measure the pressure transmitted from a contact portion of the subject's body 100 and the optical pulse wave measuring unit 16, the fixing units 12a and 12b may be formed of a material which does not absorb the pressure. The fixing units 12a and 12b may be formed as a structure including a first insulating layer, a conductive layer, and a second insulating layer, which are disposed on the lower structure 10, and the conductive layer may be an electrode structure which is patterned with a metal or a conductive material. The fixing units 12a and 12b may be formed of a rigid printed circuit board (RPCB).

The ends of the pressure pulse wave measuring unit 14 are supported by the fixing units 12a and 12b, which are each connected to an end of the pressure pulse wave measuring unit 14. In this way, the pressure pulse wave measuring unit 14 can be supported by the fixing units 12a and 12b such that it is raised above and separate from the lower structure 10. The pressure pulse wave measuring unit 14 may be formed of a flexible material that can be deformed by pressure from the subject's body 100. The pressure pulse wave measuring unit 14 may include a conductive material layer which is capable of transmitting a bio-signal or of supplying power. In addition, a passivation layer, which is coated with an insulating material, may be disposed on the conductive material layer.

In order to measure a pressure applied to the pressure pulse wave measuring unit 14 via the optical pulse wave measuring unit 16, as a surface of the subject's body 100 is brought into contact with the optical pulse wave measuring unit 16, the pressure pulse wave measuring unit 14 may be formed of a flexible material, and a change in the resistance of the pressure pulse wave measuring unit 14 may be measured as it relates to the downward warpage of the pressure pulse wave measuring unit 14. The pressure pulse wave measuring unit 14 may be formed of an elastic and resilient material, such that it is restored to its original shape after the subject's body 100 and the optical pulse wave measuring unit 16 are separated from each other. For example, the pressure pulse wave measuring unit 14 may be formed of a flexible printed circuit board (FPCB). A width and thickness of the pressure pulse wave measuring unit 14 are not limited to particular values and may be within a range of dozens of micrometers (μm) to dozens of millimeters (mm).

The optical pulse wave measuring unit 16 may be disposed on the pressure pulse wave measuring unit 14 and an upper surface of the optical pulse wave measuring unit 16 may be configured to be brought into contact with a surface of a subject's body 100. When the surface of the subject's body 100 contacts the upper surface of the optical pulse wave measuring unit 16, the optical pulse wave measuring unit 16 may measure an optical pulse wave of the subject's body 100, and at the same time, may transmit a pressure, applied to the optical pulse wave measuring unit 16 from the subject's body, to the pressure pulse wave measuring unit 14.

The optical pulse wave measuring unit 16 may include a light-emitting portion and a light-receiving portion to measure an optical pulse wave of a contact portion of the subject's body. When light is irradiated, from the light-emitting portion of the optical pulse wave measuring unit 16 and onto the surface of the subject's body 100 contacting the optical pulse wave measuring unit 16, some of the irradiated light may be absorbed by a blood vessel of the subject's body 100 and the rest of the irradiated light may be reflected. The optical pulse wave may be measured by measuring the amount of reflected light by using the light-receiving portion of the optical pulse wave measuring unit 16. A light-emitting diode (LED) may be used as a light source of the light-emitting portion of the optical pulse wave measuring unit 16. A photodiode or a photo transistor (PTR) may be used as the light-receiving portion of the optical pulse wave measuring unit 16.

A size of the optical pulse wave measuring unit 16 is not limited and the optical pulse wave measuring unit 16 may be configured to have a size within a range of dozens of micrometers (μm) to dozens of millimeters (mm) to enable the unit 16 to easily contact the subject's body 100, while also disposed on the pressure pulse wave measuring unit 14. To transmit the pressure, generated by the contact of the optical pulse wave measuring unit 16 and the subject's body 100, to the pressure pulse wave measuring unit 14 disposed below the optical pulse wave measuring unit 16, the optical pulse wave measuring unit 16 may be formed of a material which does not absorb the pressure generated by the contact of the subject 100 and the optical pulse wave measuring unit 16. Also, the optical pulse wave measuring unit 16 may be configured such that its upper surface protrudes upwards from the upper surfaces of the fixing units 12a and 12b. The optical pulse wave measuring unit 16 may be disposed on a central portion of the pressure pulse wave measuring unit 14 and may share a central axis, in a vertical direction, of the pressure pulse wave measuring unit 14.

The subject's body 100, which is an object of the biometric information detection, may be a portion of a living subject's body which may contact the optical pulse wave measuring unit 16 of the biometric information detecting apparatus, or may be a portion of a subject's body on which it is easy to measure a pulse wave by photoplethysmography (PPG). For example, the subject's body 100 may be a portion of a subject's wrist surface that is proximate to the radial artery. However, the subject's body 100 is not limited thereto and may be any of various other parts of a subject's body including, for example any of distal parts of a subject's body, such as the fingers, the toes, the earlobes, etc., which have a high vascular density.

According to exemplary embodiments, a biometric information detecting apparatus may be configured to measure, with respect to a single portion of the subject's body, both a pressure pulse wave, measured by the pressure pulse wave measuring unit 14 according to a pressure change of a surface of a subject's body 100, and an optical pulse wave measured by the optical pulse wave measuring unit 16 by receiving light which passes through the subject's body 100 and is reflected.

Waveforms of the pressure pulse wave detected by the pressure pulse wave measuring unit 14 may differ from those of the optical pulse wave detected by the optical pulse wave measuring unit 16. The pulse wave measuring error of the subject's body 100 may be minimized by simultaneously measuring both the pressure pulse wave and the optical pulse wave for pulse wave analysis (PWA).

Figure 2A:
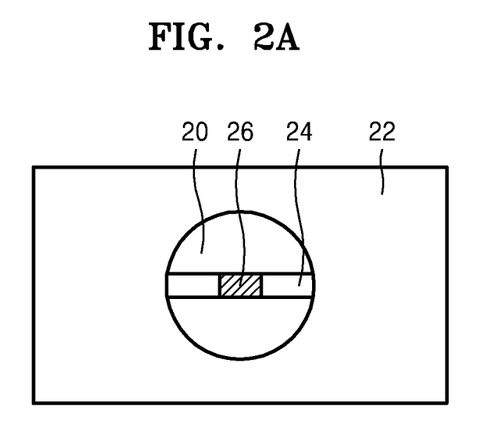
FIGS. 2A and 2B are plan views of biometric information detecting apparatuses according to other exemplary embodiments.
Figure 2B:
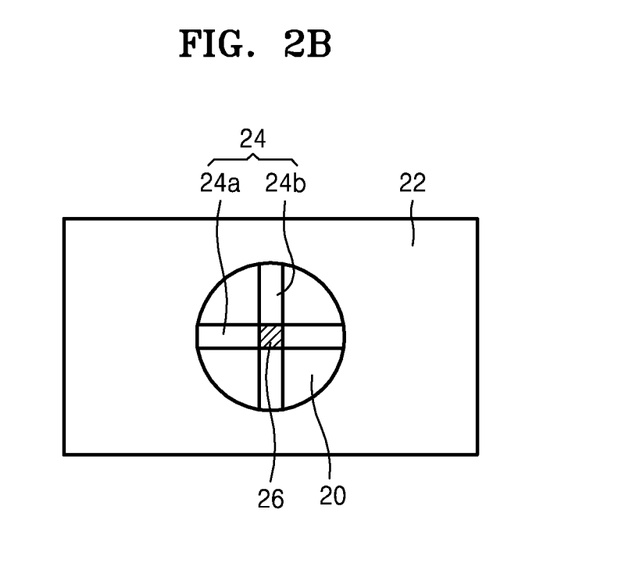

FIGS. 2A and 2B are upper plan views of biometric information detecting apparatuses according to other exemplary embodiments.

Referring to FIG. 2A, a hole is formed in a portion of a fixing unit 22 to expose a surface of a lower structure 20. A pressure pulse wave measuring unit 24 may be disposed in the hole of the fixing unit 22. That is, opposite ends of the pressure pulse wave measuring unit 24 may be fixed within the hole of the fixing unit 22 and an optical pulse wave measuring unit 26 may be disposed on the pressure pulse wave measuring unit 24. The optical pulse wave measuring unit 26 may be disposed on a central portion of the pressure pulse wave measuring unit 24. An upper surface of the optical pulse wave measuring unit 26 may be configured to extend above an upper surface of the fixing unit 22, and the upper surface of the optical pulse wave measuring unit 26 may protrude outwards from the upper surface of the fixing unit 22.

Referring to FIG. 2B, a hole is formed in a portion of the fixing unit 22 to expose a surface of the lower structure 20. The pressure pulse wave measuring unit 24, including a plurality of pattern portions 24a and 24b, may be disposed in the hole of the fixing unit 22. Ends of the pattern portions 24a and 24b of the pressure pulse wave measuring unit 24 may be fixed within side wall portions of the hole of the fixing unit 22, and the optical pulse wave measuring unit 26 may be disposed on the pressure pulse wave measuring unit 24.

FIG. 2A illustrates a biometric information detecting apparatus including a pressure pulse wave measuring unit 24 that includes two pattern portions, and FIG. 2B illustrates that a biometric information detecting apparatus including a pressure pulse wave measuring unit 24 that includes four pattern portions. Thus, the pressure pulse wave measuring unit 24 may include one or more pattern portions, for example, two pattern portions or four pattern portions. The optical pulse wave measuring unit 26 may be disposed on the central portion of the pressure pulse wave measuring unit 24. The optical pulse wave measuring unit 26 may be configured such that its upper surface extends higher than an upper surface of the fixing unit 22. The upper surface of the optical pulse wave measuring unit 26 may protrude outwards from the upper surface of the fixing unit 22.

Figure 3A:
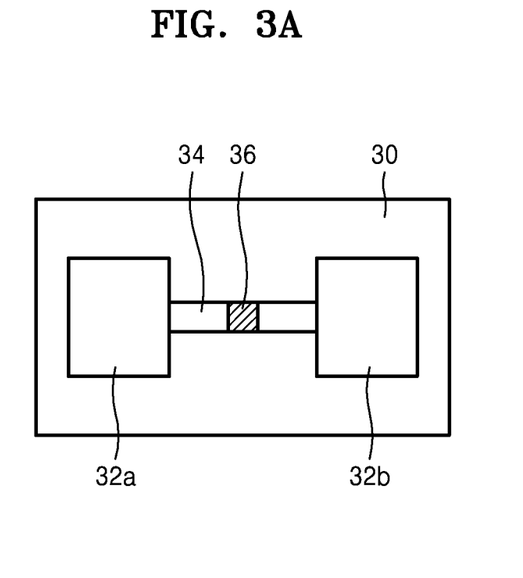
FIGS. 3A and 3B are plan views of biometric information detecting apparatuses according to other exemplary embodiments.
Figure 3B:
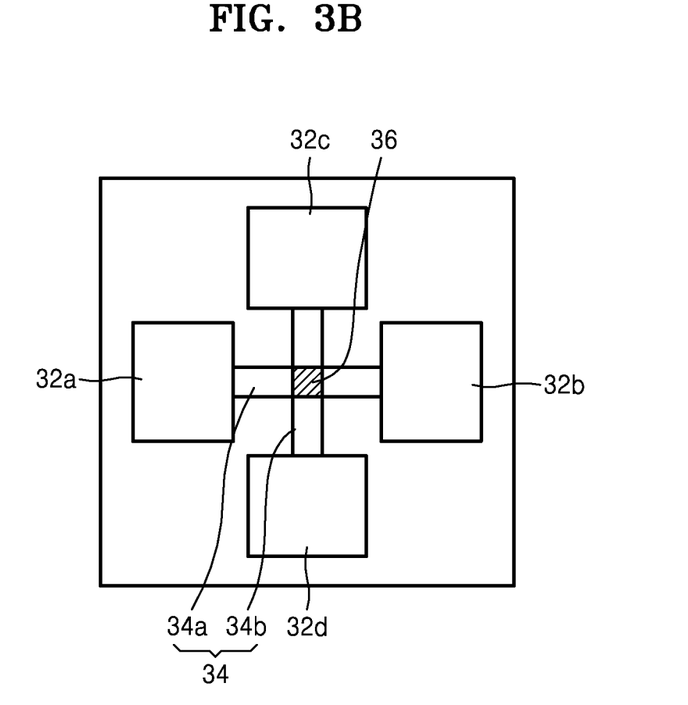

FIGS. 3A and 3B are upper plan views of biometric information detecting apparatuses according to other exemplary embodiments.

Although FIGS. 2A and 2B illustrate embodiments in which the pattern portions of the pressure pulse wave measuring unit 24 are fixed within the hole of one fixing unit, FIGS. 3A and 3B illustrate embodiments in which pattern portions of a pressure pulse wave measuring unit 34 are respectively connected to different fixing units.

Referring to FIG. 3A, fixing units 32a and 32b are each independently disposed on a lower structure 30, and the pressure pulse wave measuring unit 34 may be disposed between the fixing units 32a and 32b. Also, an optical pulse wave measuring unit 36 may be disposed on a portion of the pressure pulse wave measuring unit 34. The pressure pulse wave measuring unit 34 may be configured such that opposite ends of the unit 34 are respectively connected to the fixing units 32a and 32b. Here, although it is illustrated that the pressure pulse wave measuring unit 34 includes two ends, exemplary embodiments are not limited thereto.

Referring to FIG. 3B, a plurality of fixing units 32a, 32b, 32c, and 32d are each independently disposed on the lower structure 30 and the pressure pulse wave measuring unit 34 is disposed between the fixing units 32a, 32b, 32c, and 32d.

Also, the optical pulse wave measuring unit 36 is disposed on a portion of the pressure pulse wave measuring unit 34. Ends of a plurality of pattern portions 34a and 34b of the pressure pulse wave measuring unit 34 may be connected to the fixing units 32a, 32b, 32c, and 32d which are each independently disposed on the lower structure 30. Thus, as shown, the pressure pulse wave measuring unit 34 may include one or more pattern portions.

Figure 4:
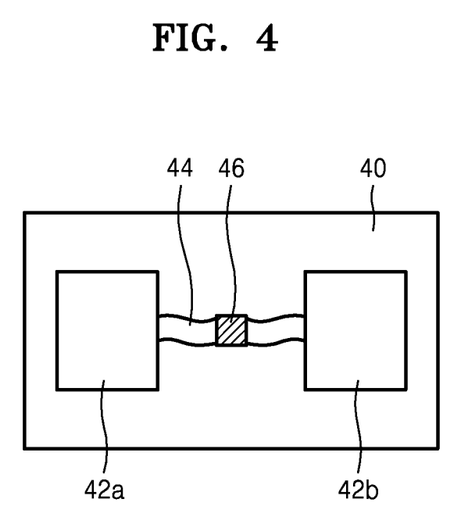
FIG. 4 is a plan view of a biometric information detecting apparatus including a pressure pulse wave measuring unit that is formed in a non-linear structure.

FIG. 4 is a plan view of a biometric information detecting apparatus including a pressure pulse wave measuring unit 44 that includes a non-linear structure Referring to FIG. 4, fixing units 42a and 42b are disposed on a lower structure 40, and a pressure pulse wave measuring unit 44 is connected to the fixing units 42a and 42b and separate from the lower structure 40. An optical pulse wave measuring unit 46 is disposed on the pressure pulse wave measuring unit 44. The pressure pulse wave measuring unit 44 may include pattern portions connected with the fixing units 42a and 42b, and the pattern portions may have any of various shapes. FIG. 1 illustrates an embodiment in which a pattern portion (not shown) of the pressure pulse wave measuring unit 14 has a straight shape, and FIG. 4 illustrates an embodiment in which the pressure pulse wave measuring unit 44 includes pattern portions having curvature, such that the pattern portions each have an S-shape. The shape of the pressure pulse wave measuring unit 44 is not limited thereto. For example, the pressure pulse wave measuring unit 44 may have a zigzag shape.

Figure 5:
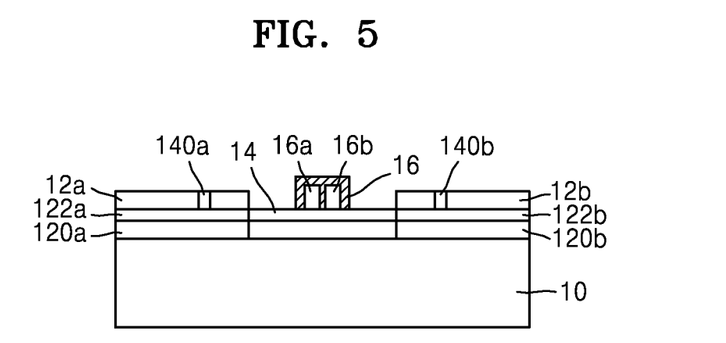
FIG. 5 is a cross-sectional view of a biometric information detecting apparatus in which an optical pulse wave measuring unit includes a light-emitting device portion and a light-receiving device portion, according to an exemplary embodiment.

FIG. 5 is a cross-sectional view of a biometric information detecting apparatus in which the optical pulse wave measuring unit 16 includes a light-emitting device portion and a light-receiving device portion, according to an exemplary embodiment.

Referring to FIG. 5, the fixing units 12a and 12b may be disposed on the lower structure 10. The pressure pulse wave measuring unit 14, which is separate from the lower structure 10 and supported by the fixing units 12a and 12b, may be disposed between the fixing units 12a and 12b. The optical pulse wave measuring unit 16 may be disposed on the pressure pulse wave measuring unit 14. The fixing units 12a and 12b supporting the pressure pulse wave measuring unit 14 may include conductive patterns 122a and 122b, which are capable of receiving bio-signals from the pressure pulse wave measuring unit 14 and the optical pulse wave measuring unit 16 or of supplying power to the pressure pulse wave measuring unit 14 and to the optical pulse wave measuring unit 16. The conductive patterns 122a and 122b of the fixing units 12a and 12b may be mounted on insulating layers 120a and 120b, and the fixing units 12a and 12b may further include plugs 140a and 140b, which are electrically connected to the conductive patterns 122a and 122b to transmit signals or to supply power.

The optical pulse wave measuring unit 16 may include a light-emitting portion 16a and a light-receiving portion 16b. The light-emitting portion 16a may be an LED and the light-receiving portion 16b may be a photodiode or a PTR.

Figure 6:
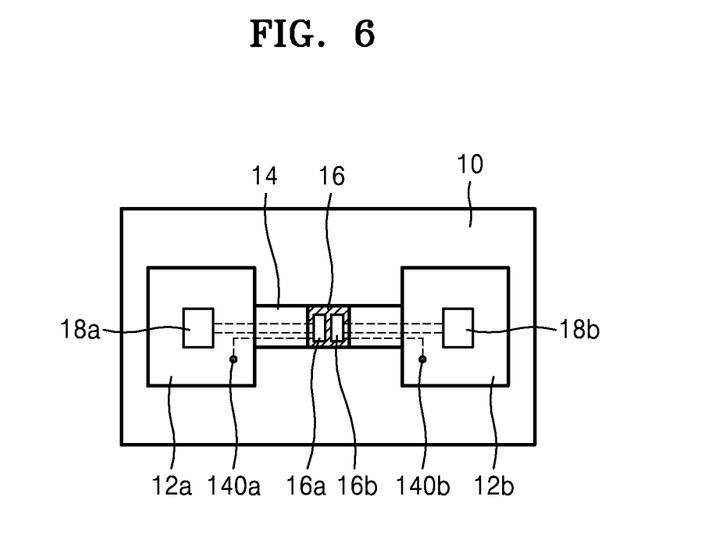
FIG. 6 is a plan view of a biometric information detecting apparatus including an optical pulse wave measuring unit and a pressure pulse wave measuring unit having a wiring structure, according to an exemplary embodiment.

FIG. 6 is a plan view of a biometric information detecting apparatus including the optical pulse wave measuring unit 16 and the pressure pulse wave measuring unit 14 having a wiring structure, according to an exemplary embodiment.

FIG. 6 illustrates a structure in which optical signal measuring portions, for example, a light-emitting device control portion 18a and a light-receiving device control portion 18b, connected with the optical pulse wave measuring unit 16, are disposed on the fixing units 12a and 12b.

Referring to FIG. 6, a biometric information detecting apparatus includes the light-emitting device control portion 18a electrically connected to the light-emitting portion 16a of the optical pulse wave measuring unit 16 and the light-receiving device control portion 18b electrically connected with the light-receiving portion 16b of the optical pulse wave measuring unit 16. The light-emitting device control portion 18a and the light-receiving device control portion 18b may be disposed on the fixing units 12a and 12b, respectively. Alternately, positions of the light-emitting device control portion 18a and the light-receiving device control portion may be determined such that the light-emitting device control portion 18a and the light-receiving device control portion 18b are disposed on portions of the lower structure, instead of being formed on the fixing units 12a and 12b. A light-emitting device of the light-emitting portion 16a may be controlled by the light-emitting device control portion 18a, and a light-receiving signal measured by the light-receiving portion 16b may be amplified and stored by the light-receiving device control portion 18b. Pressure signals from the subject's body 100 and the pressure pulse wave measuring unit 14 may be measured by using the conductive patterns 122a and 122b or plugs 140a and 140b of FIGS. 4 and 5, and the pressure signals may be stored by converting a resistance signal change of the pressure pulse wave measuring unit 14 into a voltage value.

As described above, according to one or more exemplary embodiments, both a pressure pulse wave and an optical pulse wave may be easily measured from the same portion of a subject's body. Thus, measurement errors of the optical pulse wave and of the pressure pulse wave may be minimized, and a precise value of biometric information may be detected. According to exemplary embodiments, the optical pulse wave and the pressure pulse wave are simultaneously measured from an identical portion of the subject's body, and thus, the biometric information such as a pulse wave may be precisely measured. A biometric information detecting apparatus according to one or more exemplary embodiments may be used in any of various wearable devices such as smart watches.

It should be understood that the exemplary embodiments described herein should be considered in a descriptive sense only and not for purposes of limitation. Descriptions of features or aspects within each embodiment should typically be considered as available for other similar features or aspects in other embodiments. It will be understood that the above descriptions of exemplary embodiments may be applied to other electronic devices for health care, in addition to wearable devices.

While exemplary embodiments have been described with reference to the figures, it will be understood by those of ordinary skill in the art that various changes in form and details may be made herein without departing from the spirit and scope of the present invention as defined by the following claims.

What is claimed is:

1. A biometric information detecting apparatus comprising:
   a fixing unit disposed on a lower structure;
   a pressure pulse wave measuring unit connected to the fixing unit and spaced apart from the lower structure; and
   an optical pulse wave measuring unit disposed on the pressure pulse wave measuring unit,
   wherein the fixing unit comprises a substrate having a hole formed therein, a surface of the lower structure being exposed by the hole, and
   wherein a first end portion and a second end portion of the pressure pulse wave measuring unit are respectively connected to inner side walls of the hole, the inner side walls extending in a direction that crosses a direction in which the pressure pulse wave measuring unit extends.

2. The biometric information detecting apparatus of claim 1, wherein the optical pulse wave measuring unit is configured such that an upper surface of the optical pulse wave measuring unit is in a position to directly contact a subject's body.

3. The biometric information detecting apparatus of claim 1, wherein an upper surface of the optical pulse wave measuring unit protrudes above an uppermost surface of the fixing unit.

4. The biometric information detecting apparatus of claim 1, wherein the pressure pulse wave measuring unit is disposed such that the pressure pulse wave measuring unit is separate from the lower structure.

5. The biometric information detecting apparatus of claim 4, the pressure pulse wave measuring unit comprises a flexible material.

6. The biometric information detecting apparatus of claim 1, wherein the fixing unit comprises at least one fixing unit respectively connected to at least one end of the pressure pulse wave measuring unit.

7. The biometric information detecting apparatus of claim 6, wherein the pressure pulse wave measuring unit comprises at least one pattern portion respectively connected to the at least one fixing unit, wherein each of the at least one pattern portion has at least one of a straight, linear shape; a curved shape; and a zigzag shape.

8. The biometric information detecting apparatus of claim 1, wherein the fixing unit comprises a rigid printed circuit board and the pressure pulse wave measuring unit comprises a flexible printed circuit board.

9. The biometric information detecting apparatus of claim 1, wherein the pressure pulse wave measuring unit comprises at least one pattern portion connected to a side wall of the hole, and each of the at least one pattern portion has at least one of a straight, linear shape; a curved shape; and a zigzag shape.

10. The biometric information detecting apparatus of claim 1, wherein the optical pulse wave measuring unit is disposed on a central portion of the pressure pulse wave measuring unit; and
the optical pulse wave measuring unit is configured to measure an optical pulse wave with respect to a region of a subject's body, and the pressure pulse wave measuring unit is configured to measure a pressure pulse wave with respect to the region of the subject's body, when the optical pulse wave measuring unit is in contact with the region of the subject's body.

11. The biometric information detecting apparatus of claim 1, wherein a central axis of the optical pulse wave measuring unit is aligned, in a vertical direction, with a central axis of the pressure pulse wave measuring unit.

12. The biometric information detecting apparatus of claim 1, wherein the optical pulse wave measuring unit comprises a light-receiving portion and a light-emitting portion.

13. The biometric information detecting apparatus of claim 12, wherein the optical pulse wave measuring unit is electrically connected to an optical signal measuring unit via the pressure pulse wave measuring unit.

14. The biometric information detecting apparatus of claim 13, wherein the optical signal measuring unit comprises a light-emitting device control portion, which is electrically connected to the light-emitting portion, and a light-receiving device control portion which is electrically connected to the light-receiving portion.

15. The biometric information detecting apparatus of claim 14, wherein the light-emitting device control portion is disposed on the fixing unit, and the light-receiving device control portion is disposed on the fixing unit.

16. The biometric information detecting apparatus of claim 1, wherein the fixing unit comprises a conductive pattern and is configured to perform at least one of:
receiving a bio-signal from at least one of the pressure pulse wave measuring unit and the optical pulse wave measuring unit; and
supplying power to at least one of the pressure pulse wave measuring unit and the optical pulse wave measuring unit.

17. The biometric information detecting apparatus of claim 16, wherein the fixing unit comprises the conductive pattern mounted on an insulating layer.

18. The biometric information detecting apparatus of claim 17, wherein the fixing unit further comprises a plug which is electrically connected to the conductive pattern.

19. A biometric information detecting apparatus comprising:
a fixing unit disposed on a lower structure;
a pressure pulse measuring unit comprising a flexible material and connected to the fixing unit and spaced apart from the lower structure, and
an optical pulse wave measuring unit comprising a light emitting portion and a light receiving portion, wherein the optical pulse wave measuring unit is disposed on the flexible material and protrudes thereabove, such that pressure applied to an upper surface of the optical pulse wave measuring unit is transmitted through the optical pulse wave measuring unit to the flexible material,
wherein the fixing unit comprises a substrate having a hole formed therein, a surface of the lower structure being exposed by the hole, and
wherein a first end portion and a second end portion of the pressure pulse measuring unit are respectively connected to inner side walls of the hole, the inner side walls extending in a direction that crosses a direction in which the pressure pulse measuring unit extends.

20. A biometric information detecting apparatus comprising:
a fixing unit disposed on a lower structure;
a pressure pulse wave measuring unit connected to inner side walls of the fixing unit, wherein the pressure pulse wave measuring unit comprises a flexible material and is spaced apart from the lower structure, the inner side walls extending in a direction that crosses a direction in which the pressure pulse wave measuring unit extends; and
an optical pulse wave measuring unit disposed on the pressure pulse wave measuring unit.

* * * * *